United States Patent
Lambert et al.

(10) Patent No.: US 6,588,253 B2
(45) Date of Patent: Jul. 8, 2003

(54) FUEL VOLATITLITY SENSOR AND METHOD BASED ON CAPACITANCE MEASUREMENT

(75) Inventors: David K. Lambert, Sterling Heights, MI (US); Charles Robert Harrington, Troy, MI (US); Han-Sheng Lee, Bloomfield Hills, MI (US); Da Yu Wang, Troy, MI (US)

(73) Assignee: Delphi Technologies, Inc., Troy, MI (US)

( * ) Notice: Subject to any disclaimer, the term of this patent is extended or adjusted under 35 U.S.C. 154(b) by 158 days.

(21) Appl. No.: 09/932,333

(22) Filed: Aug. 17, 2001

(65) Prior Publication Data

US 2003/0033858 A1 Feb. 20, 2003

(51) Int. Cl.[7] .................. F02D 45/00; F02D 19/08; F02D 41/00; G01N 25/48; G01N 25/02
(52) U.S. Cl. .............. 73/53.01; 73/61.41; 73/61.46; 73/61.77; 324/71.1; 324/690; 137/341
(58) Field of Search .................. 73/53.01, 61.41, 73/61.46, 61.77; 324/71.1, 664, 670, 690; 137/341, 559

(56) References Cited

U.S. PATENT DOCUMENTS

| | | | | |
|---|---|---|---|---|
| 3,877,639 A | * | 4/1975 | Wilson et al. | 237/12.3 C |
| 4,845,976 A | * | 7/1989 | Johnson et al. | 73/23.2 |
| 5,159,898 A | * | 11/1992 | Hartel et al. | 123/1 A |
| 5,182,942 A | * | 2/1993 | Hartel et al. | 73/61.46 |
| 5,423,206 A | * | 6/1995 | Hetzel | 73/61.77 |
| 5,646,539 A | * | 7/1997 | Codina et al. | 324/678 |
| 5,832,921 A | * | 11/1998 | Lennert et al. | 128/632 |
| 5,915,368 A | * | 6/1999 | Ishida et al. | 123/675 |
| 6,078,861 A | * | 6/2000 | Zimmerman et al. | 701/114 |

FOREIGN PATENT DOCUMENTS

DE 4019188 A1 * 12/1990 ........... F02D/19/08

* cited by examiner

Primary Examiner—Helen Kwok
Assistant Examiner—David Wiggins
(74) Attorney, Agent, or Firm—Margaret A. Dobrowitsky

(57) ABSTRACT

A method and apparatus for determining a volatility of a fuel sample. A fuel sample is collected in a container and heated for a time period using a heater device. Periodically during the heating, the capacitance of the fuel sample and the temperature of the heater device are determined. After a time period passes, the volatility of the fuel sample is determined using the capacitance decrease and the temperature increase. Specifically, a voltage across the heater device is used, along with the current through the heater device to determine the resistance of the heater device, which gives the temperature of the heater device and the sample. The capacitance and temperature are compared to values derived from experimentation for fuels of varying DI. The first measurement of capacitance with a known sample volume can be used to determine the MTBE or ethanol content in gasoline fuels.

21 Claims, 4 Drawing Sheets

FUEL VOLATITLITY SENSOR AND METHOD BASED ON CAPACITANCE MEASUREMENT

TECHNICAL FIELD

The invention relates in general to an apparatus and method for determining the volatility of a fuel.

BACKGROUND OF THE INVENTION

It is known in the art relating to automotive engines that a key gasoline characteristic for good driveability during the cold start period of engine operation is volatility. Volatility is especially important at the time an engine is started because the oxygen sensor is too cold to allow closed-loop control of the air-to-fuel ratio, the catalytic converter is too cold to efficiently oxidize hydrocarbon emissions in the exhaust, and because the intake manifold is too cold to rapidly evaporate all of the fuel that is injected. If too little gasoline is injected relative to the air intake, the engine has poor driveability; if too much gasoline is injected relative to the air intake, then extra hydrocarbons from an unburned portion of gasoline are found in the exhaust. Because gasoline sold in the United States varies in volatility, there is a tradeoff in engine design between low hydrocarbon emissions and good driveability with low volatility fuel.

To describe the effect of gasoline volatility on the cold start and warm-up driveability of a vehicle, a driveability index ("DI") has been developed. Fuel with low DI is more volatile than fuel with high DI. In the United States, fuel is sold with DI that ranges from 910 to 1320. After being dispensed into a vehicle, fuel weathers as the more volatile constituents preferentially evaporate. This causes its DI to increase. Vehicle manufacturers take this wide variation in fuel DI into account. Engines are designed to meet requirements for low total emissions of hydrocarbons in the exhaust during the federal test procedure ("FTP test"), performed with tightly controlled calibration fuel, but engines should also provide satisfactory performance with the fuels that are actually used. Accurate control of the air-to-fuel ratio during the cold start period of engine operation helps achieve both of these goals. During the cold start period the air-to-fuel ratio is set in open loop control. Unfortunately, variation in the DI of fuel used in the United States limits the accuracy of open loop control of the air-to-fuel ratio during the cold start period since the intake manifold has not yet warmed up enough to evaporate all of the fuel that is injected.

Vehicle manufacturers presently address this problem in two ways. The first is to calibrate the engine fueling algorithm to provide extra fuel, so that acceptable cold start performance is experienced even with fuel that has volatility near the low end of the range encountered in the real world. One drawback of this approach is that it increases the vehicle's exhaust hydrocarbon emissions on the FTP test. A large fraction of the remaining exhaust hydrocarbon emissions occur during the cold start period of engine operation. There is need for a cost effective way to decrease these emissions and meet the more stringent emission regulations coming into effect.

The second approach is to provide two calibrations for the engine. The default calibration is intended for use with the certification fuel used on the FTP test. A secondary calibration is provided that adds extra fuel to provide good engine performance with low volatility fuel, but causes higher exhaust hydrocarbon emissions. The engine is monitored during the cold start period for symptoms that are indicative of operation with high DI fuel. If such symptoms are detected, the engine switches from the default calibration to the secondary calibration. Thus, for the FTP test with certification fuel, the default calibration is used to obtain acceptably low exhaust hydrocarbon emissions. For real world operation with low volatility fuel, one symptom of a fuel-related problem triggers the use of the secondary fueling algorithm. Engine performance is adequate after the switch, but exhaust hydrocarbon emissions are increased.

If the volatility of the fuel (DI) were known from an on-board sensor then it would be possible to use the information to improve open-loop control of the air-to-fuel ratio. This would decrease exhaust hydrocarbon emissions, improve engine performance during the cold start period, decrease the delays associated with engine development, and improve fuel economy.

SUMMARY OF THE INVENTION

The present invention provides a method and apparatus for determining the volatility, specifically the driveability index, of a fuel to control engine operation based on measurements of capacitance obtained while a volume of fuel is heated. The method for determining the volatility of a fuel sample comprises the steps of collecting the fuel sample in a container proximate to a heater device; heating the fuel sample over a time period using the heater device; measuring a capacitance of the fuel sample periodically during the step of heating the fuel sample; determining a temperature of the fuel sample periodically during the step of heating the fuel sample; and determining the volatility of the fuel sample using the capacitance and the temperature.

In one aspect, the method further comprises the step of shutting off a fuel pump of a vehicle prior to the step of heating the fuel sample. This aspect can further include the step of storing a value for the volatility of the fuel sample until an ignition of the vehicle is turned on.

In another aspect of the invention, the step of collecting the fuel sample in a container comprises the step of collecting the fuel sample in a cup mounted on the heater device when a fuel pump is running. The step of heating the fuel sample over a time period using the heater device, in another aspect of the invention, can include the step of heating the fuel sample until a temperature of the fuel sample reaches a starting temperature plus a temperature change.

A preferred aspect of the invention exists where the step of heating the fuel sample over a time period using a heater device comprises the step of applying current to a heater of the heater device. The heater device further includes a dielectric body with a surface on which the container is mounted; a guard electrode on the surface electrically connected to the container; and two electrodes within the dielectric body operatively positioned to measure the capacitance of the fuel sample in the container. The heater is disposed within the dielectric body below the two electrodes. In this aspect, the heater is preferably a resistive heater with a known relationship of a resistance of the resistive heater to a heater temperature. In this aspect, the method can further include the step of operatively coupling a circuit to the two electrodes for measuring the capacitance of the fuel sample.

In another aspect of the invention, the step of measuring a capacitance of a fuel sample comprises the steps of operatively positioning two electrodes to measure the capacitance of the fuel sample in the container and operatively coupling a circuit to the two electrodes for-measuring the capacitance.

In yet another aspect of the invention, the step of determining a temperature of the fuel sample comprises the steps of operatively coupling a circuit to the heater device for measuring a voltage drop across the heater device; determining a resistance of the heater device using the voltage drop and a current applied to the heater device; and determining a heater temperature of the heater device based on a known relationship between the resistance of the heater device and the heater temperature; and wherein the heater temperature is the temperature of the fuel sample.

In the method of the present invention, the step of determining the volatility of the fuel sample using the capacitance and the temperature can comprise the step of comparing the capacitance and the temperature to experimental values for fuels with a variety of volatilities.

The method can optionally include the step of using a first measurement of capacitance to detect a concentration of oxygenate in the fuel sample. In a preferred aspect of the invention, the step of determining the volatility of the fuel sample comprises the step of determining a driveability index of the fuel sample.

The apparatus for determining a volatility of a fuel sample comprises a container for collecting the fuel sample proximate to a heater device, the heater device heating the fuel sample over a time period; means for measuring a capacitance of the fuel sample periodically during the step of heating the fuel sample; means for determining a temperature of the fuel sample periodically during the step of heating the fuel sample; and means for determining the volatility of the fuel sample using the capacitance and the temperature. Preferably, the container is a cup mounted on the heater device collecting the fuel sample when a fuel pump is running.

In one aspect of the invention, the heater device comprises a dielectric body with a surface on which the container is mounted; a guard electrode on the surface electrically connected to the container; two electrodes within the dielectric body operatively positioned to measure the capacitance of the fuel sample in the container; and a heater disposed within the dielectric body below the two electrodes. The heater is preferably a resistive heater with a known relationship of a resistance of the resistive heater to a heater temperature. In yet another aspect, this apparatus further includes a circuit operatively coupled to the two electrodes for measuring the capacitance of the fuel sample.

In another aspect of the invention, the means for measuring a capacitance of a fuel sample comprises two electrodes operatively positioned to measure the capacitance of the fuel sample in the container and a circuit operatively coupled to the two electrodes for measuring the capacitance.

In yet another aspect of the invention, the means for determining a temperature of the fuel sample comprises a circuit operatively coupled to the heater device for measuring a voltage drop across the heater device; means for determining a resistance of the heater device using the voltage drop and a current applied to the heater device; and means for determining a heater temperature of the heater device based on a known relationship between the resistance of the heater device and the heater temperature. The heater temperature is the temperature of the fuel sample.

In another aspect of the apparatus of the invention, the means for determining the volatility of the fuel sample using the capacitance and the temperature comprises means for comparing the capacitance and the temperature to experimental values for fuels with a variety of volatilities.

BRIEF DESCRIPTION OF THE DRAWING

The various features, advantages and other uses of the present invention will become more apparent by referring to the following detailed description and drawings in which like numerals refer to like and in which.

DETAILED DESCRIPTION

Figure 1:
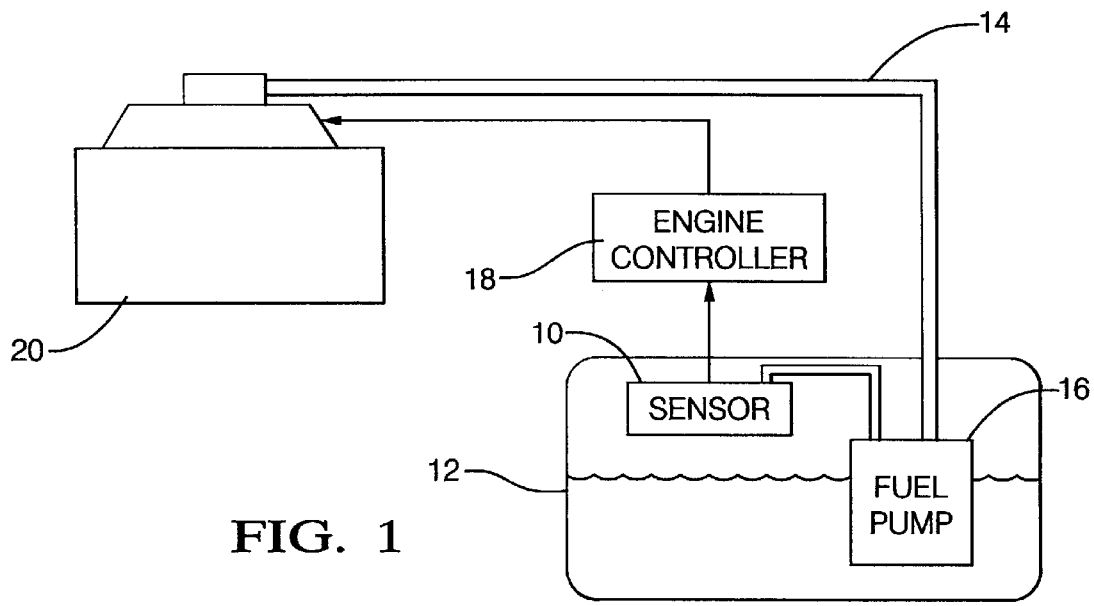
FIG. 1 is a diagram showing the sensor of the present invention in relationship to an engine, an engine controller and fuel tank and fuel pump of a vehicle.

Referring now to the drawing in detail, particularly to FIGS. 1 to 6, shown are the sensor apparatus and method of the present invention. As shown in FIG. 1, the sensor 10 is preferably incorporated into an engine control system. Specifically, the sensor 10 is located in the fuel tank 12 of a vehicle (not shown), and receives fuel continuously while the fuel pump 16 is powered on during engine operation. In the aspect shown, the fuel sensor 10 receives fuel from the fuel pump 16, but other methods of continuously replenishing the fuel for the sensor 10 are also possible. The sensor 10 provides information, to be hereinafter discussed, to the engine controller 18. The engine controller 18 manipulates the data and controls the amount of fuel the engine 20 receives from the fuel tank 12 relative to the intake of air upon the next cold start of the engine 20.

Figure 2:
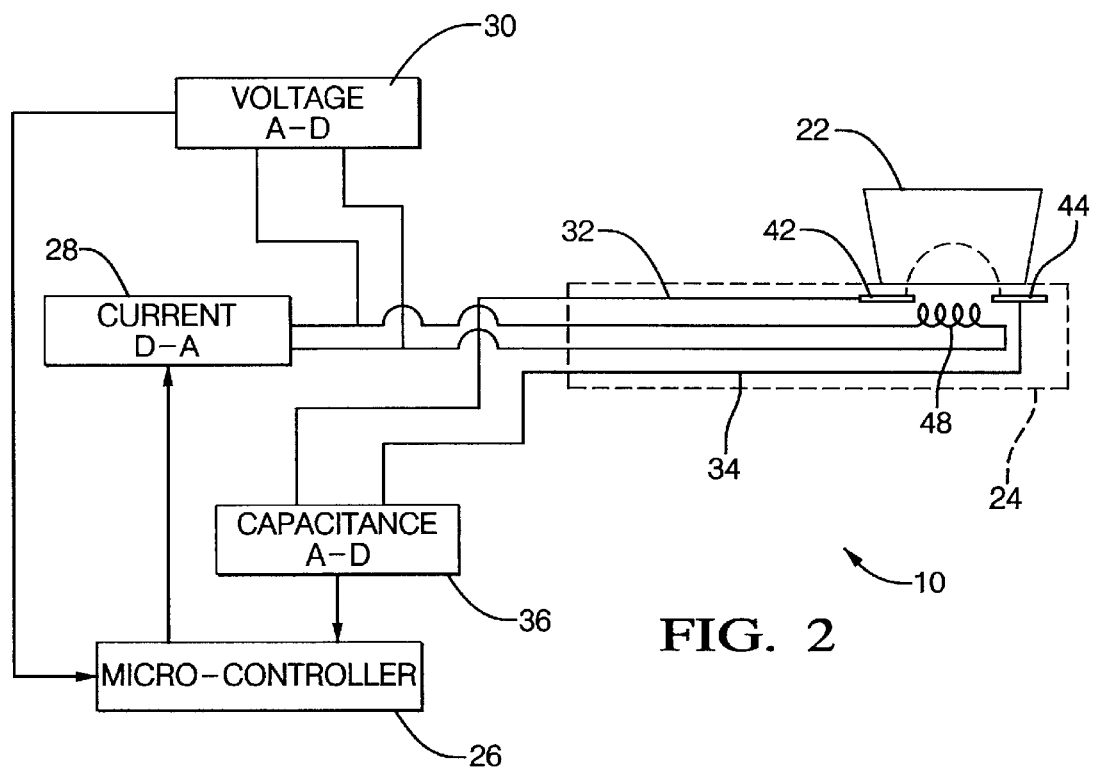
FIG. 2 is a schematic of the sensor.

The sensor 10 is shown in more detail in FIG. 2. The sensor 10 collects a sample of the fuel in a collection container or cup 22 attached to a ceramic heater/capacitor 24 with adhesive. A suitable adhesive is the 730 Solvent Resistant Sealant, a one-part flurosilicone rubber adhesive from Dow Corning Corporation of Midland, Mich. The cup 22 has an open bottom and is preferably made of a thermally conductive material such as stainless steel or brass. The thermal conductivity of the cup walls needs to be high enough to prevent evaporating fuel vapor from recondensing on the cup walls and running back down into the cup 22. Electrically conducting walls also provide one way to implement a three-terminal capacitor cell with capacitance that varies monotonically as a function of the volume of liquid fuel that remains in the cup 22. Although the collection container is shown as a cup 22 mounted to the ceramic heater/capacitor 24, the container can take other forms. Further, mounting the container to the ceramic heater/capacitor 24 is not necessary; the ceramic heater/capacitor 24 must merely be near enough to perform the described functions.

The cup 22 holds a known volume of fuel, preferably near the top of the volume range that gives approximately linear capacitance change as a function of fuel volume in the cup 22. For example, one suitable cup 22 is the cap of a TO-5 transistor package with the top drilled out, and a suitable initial volume of fuel within this cup at the beginning of the measurement is 0.06 mL. However, if such a cap is used, a conductor, such as a thin platinum wire, must be spot welded to the cap and soldered to the guard electrode 46 of the ceramic heater/capacitor 24, to be hereinafter discussed. Regardless of the material of the cup 22, if it is electrically conductive, it should have a reproducible impedance to the guard electrode 46 on the surface of the ceramic heater/capacitor 24.

A microcontroller 26 controls the current that current source 28 supplies to the heater 48 of the ceramic heater/capacitor 24 through a digital-to-analog converter. The voltage across the heater is measured by a voltage measuring circuit 30, which preferably includes a voltmeter and a converter that converts the signal from analog to digital and provides it to the microcontroller 26. Any standard voltage measuring circuit 30 is acceptable. The current from the current source 28 heats the heater 48 of the ceramic heater/capacitor 24. Additionally, capacitance measuring circuit 36 applies an alternating voltage through leads 32 and 34 at a frequency of typically 10 kHz between electrodes 42 and 44 buried in the ceramic heater/capacitor 24. This creates an electric field that passes into the cup 22. The circuit 36 then measures the resulting capacitance and converts the signal from analog to digital before it is provided to the microcontroller 26.

Figure 3:
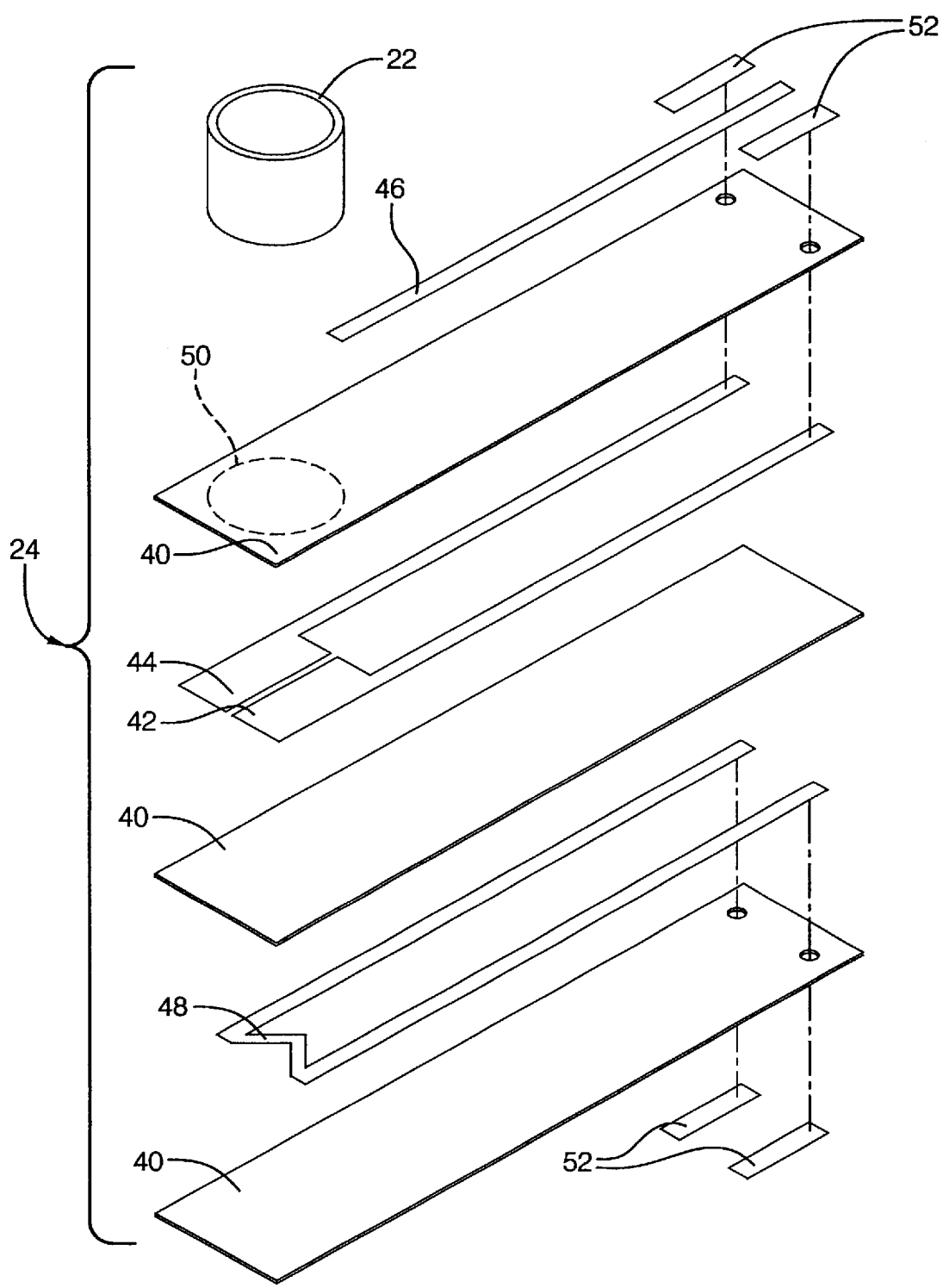
FIG. 3 is an exploded view of the ceramic heater/capacitor used in the sensor of the present invention.

An exploded view of the ceramic heater/capacitor 24 is shown in FIG. 3. The ceramic material 40 encases the capacitor electrodes 42, 44, guard electrode 46 and heater 48 previously discussed. As mentioned previously, the cup 22 is connected to the guard electrode 46. Guard electrode 46 provides electrostatic shielding between leads 32 and 34. This reduces the contribution of stray capacitance between the leads to the capacitance measured by the capacitance measuring circuit 36. The footprint 50 of the cup 22 is shown in FIG. 3. On the surface of the ceramic material 40 are contact pads 52, which provide connections to the capacitor electrodes 42, 44, to the guard electrode 46 and to the heater 48. The ceramic heater/capacitor 24 is preferably fabricated using a ceramic/tape manufacturing technology, which produces a flat-plate device.

The ceramic heater/capacitor 24 shown is fabricated as follows. First, high purity alumina powders, organic solvent, and plasticizers are combined and ball-milled into a slurry. The slurry is then cast into tapes about 190 microns thick, preferably using a doctor blade. A conductor, preferably platinum, is screen printed onto the tapes to form the conductors needed by the device, specifically the capacitor electrodes 42, 44, the guard electrode 46, the heater 48 and the contact pads 52. The layers or tapes are then thermally laminated under pressure. Finally, the tapes are cut, then fired at 1500 degrees Celsius in air for two hours.

Figure 4:
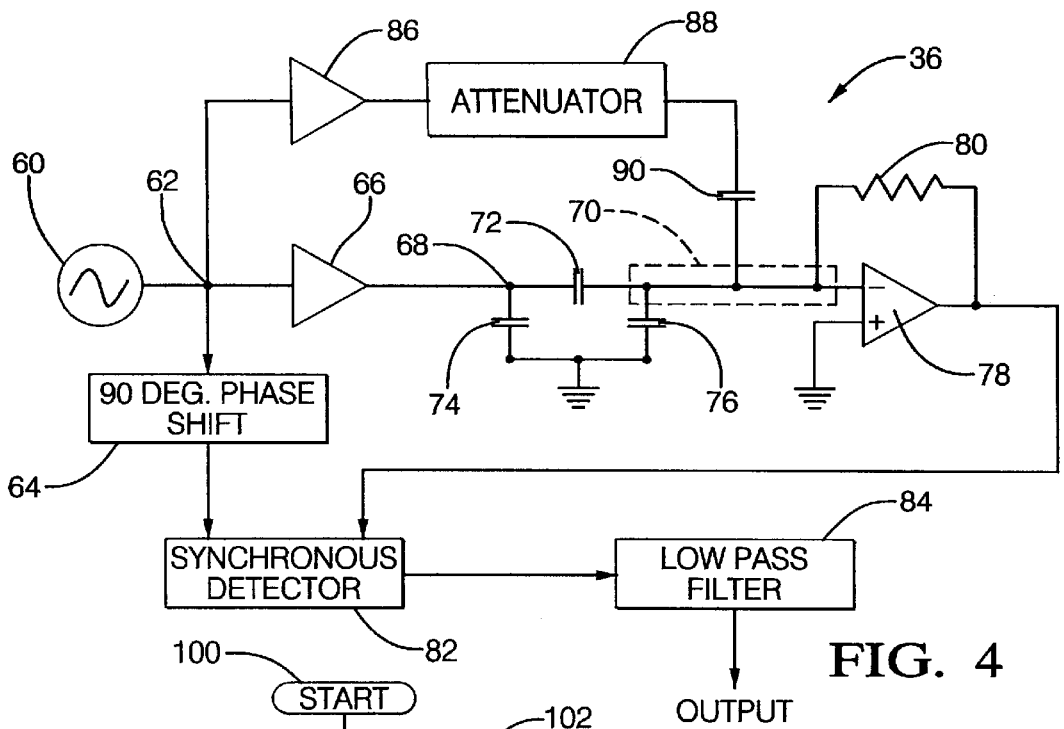
FIG. 4 is a schematic of one possible circuit used to measure the capacitance of the fluid in the fluid collector of the sensor.

One capacitance measuring circuit 36 is shown in FIG. 4. An alternating current (AC) source 60 generates a sine wave within a frequency range of typically 1 kHz to 100 kHz to node 62. The sine wave input into node 62 is supplied to a 90° phase shifter 64 wherein the sine wave is transformed into a square wave with a 90° phase shift relative to the sine wave. The square wave output of the phase shifter 64 serves as a reference input to a synchronous detector 82. The 90° phase shifter 64 can be a phase shifter of any conventional design. The sine wave supplied to node 62 is also an input to a buffer amplifier 66 with a low output impedance. The output of the buffer amplifier 66 is provided to a node 68, and then to a node 70. Between nodes 68 and 70 is the capacitance to be measured. Specifically, the unknown capacitor 72, which represents the unknown capacitance of the fluid, is connected in series from node 68 to node 70. Node 68 and node 70 are thus connected to leads 32 and 34, respectively. Two additional parasitic capacitors 74 and 76 are shown connected in parallel to ground from nodes 68 and 70, respectively. The measuring circuit is intended to be insensitive to the values of capacitors 74 and 76. Node 70 provides the inverting input to an operational amplifier (op amp) 78. The non-inverting input of the op amp 78 is grounded, and feedback is supplied through a resistor 80. Thus, node 70 is a virtual ground.

The output of the op amp 78 provides a second input to the synchronous detector 82. The synchronous detector 82 generates an output that further passes through a low pass filter 84 where undesirable high frequency noise is filtered out. The output of the low pass filter 84 indicates the change in the capacitance of capacitor 72 and is input into microcontroller 26, as previously described with reference to FIG. 2.

Additional gain elements can be inserted between the op amp 78 and the synchronous detector 82 to improve the sensitivity of the system. Also, optionally, a nulling signal can be supplied to the node 70. This is accomplished by adding an inverter 86, which receives an input signal from the AC source 60 through the node 62, an attenuator 88 receiving the output of the inverter 86, and a capacitor 90 connected in series between the attenuator 88 and the node 70.

The capacitance measuring circuit 36 shown in FIG. 4 can be implemented in off-the-shelf integrated circuits or as an application specific integrated circuit (ASIC). Although a preferred aspect is shown, the circuit 36 can be any circuit capable of measuring capacitance, for example, a capacitance bridge and a lock-in amplifier.

Figure 5:
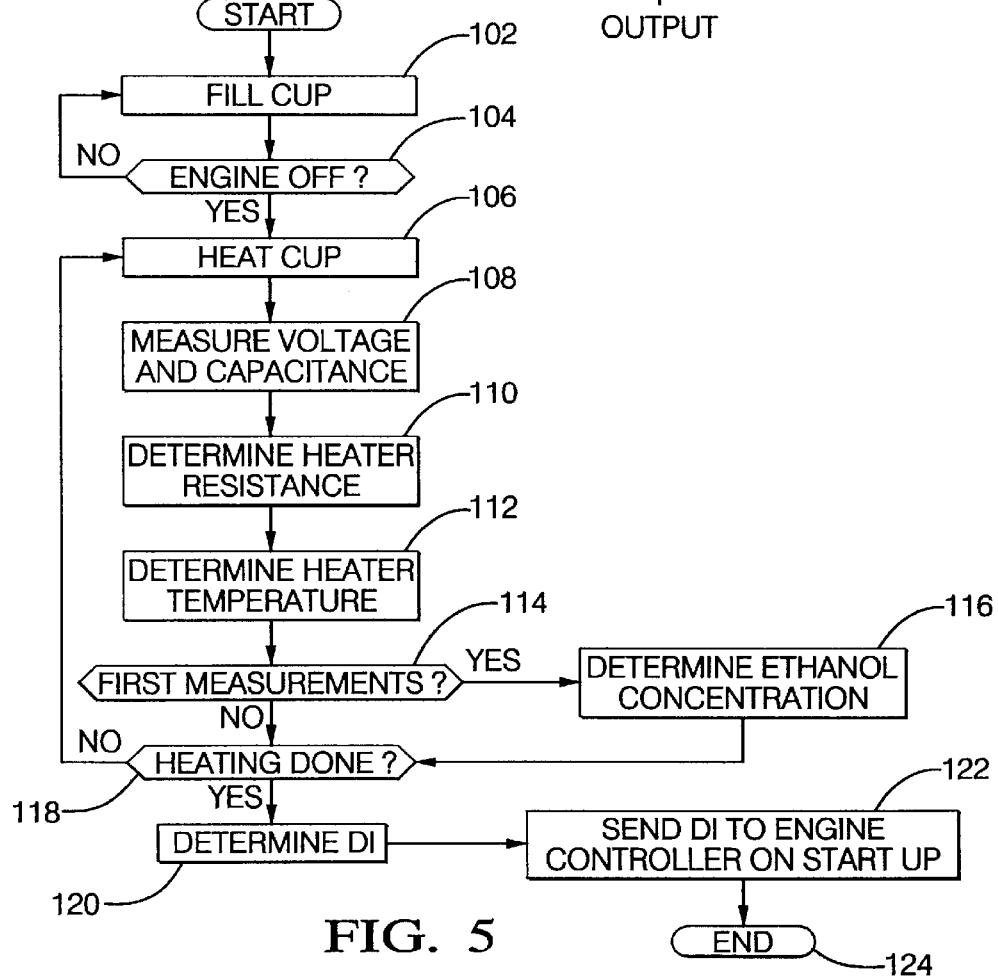
FIG. 5 is a block diagram of the method of the present invention.

A preferred aspect of the method of the present invention to determine the volatility of a fuel is shown in FIG. 5, starting at step 100. In step 102, the cup 22 is continuously replenished with fuel when the fuel pump is on. Then, the microcontroller 26 continues to query whether the engine is off in step 104. If the engine is still on then the cup continues to be replenished whenever the fuel pump is on in step 102. However, once the engine turns off in step 104, the method advances to step 106 where the sample in the cup 22 is heated by applying current to the heater 48. A predetermined hold period can be incorporated, such as 5 seconds, prior to heating the sample to allow settling of the fuel. The volume of the fuel sample when heating begins is, in most circumstances, approximately equal to the volume of the cup 22. The microcontroller 26 can control the current i through the heater 48 as a function of time t according to the formula:

$$i=i_M[(t-t_0)/\Delta t]^{1/2};$$

wherein i is the current through the heater 48;

t is the time;

$t_0$ is the starting time of the heating;

$i_M$ is the maximum current at the end of the heating, for example, 1.2 amps; and $\Delta t$ is the desired duration of the heating, for example, 500 seconds.

Although the microcontroller 26 can control the current i through the heater as a function of time according to this formula, the microcontroller 26 can also control the current through the heater according to a different function of time. Further, the microcontroller 26 can control the current through the heater 48 as a function of a different variable, such as capacitance or temperature.

During predetermined time intervals, such as twice per second, voltage is sampled by the voltage detection circuit 30 and converted from analog to digital and supplied to the microcontroller 26. In addition, the capacitance across the capacitor electrodes 42 and 44 is measured by the capacitance measuring circuit 36 and converted from analog to digital and supplied to the microcontroller 26. The measured voltage in step 108 is used to determine the resistance of the heater 48 in step 110 according to the formula:

$$R = V/i;$$

wherein

R is the resistance of the heater 48;

V is the voltage of the heater 48; and i is the current through the heater 48.

The resistance of the heater 48 has a known relationship to its temperature, preferably from a previous calibration experiment. For example, the resistance of the platinum heater 48 in the ceramic heater/capacitor 24 can be determined by placing a ceramic heater/capacitor 24 in an oven and measuring the resistance at a variety of temperatures. Alternatively, a thermocouple can be used with an empty cup 22 to measure temperature as a function of resistance as the heater 48 heats up the cup 22. Thus, step 112 can involve using a heater resistance lookup table incorporating the measured resistances and temperatures from the calibration experiment. Alternatively, step 112 can include determining the temperature from the resistance through the use of an equation, one that is either developed from the calibration experiment or is a known equation from the manufacturer of the ceramic heater/capacitor 24.

Next, the microcontroller 26 determines in step 114 whether the voltage and capacitance measurements of step 108 were the first measurements taken since the engine was turned off in step 104. If the measurements are not the first sampling in step 114, then the method proceeds to step 116. If they are the first sampling, then the concentration of an oxygenate in the fuel, such as methyl tertiary butyl ether ("MTBE") or ethanol, is determined in step 116. Electrical capacitance $C_E$ depends on the volume of fuel in the cup 22 and on the dielectric constant variable κ of the fuel, for example, gasoline. In the frequency range of interest, pure gasoline and ethanol, for example, have dielectric constants of 2.1 and 25, respectively. Measuring electrical capacitance at a known volume is an indication of the dielectric constant. As mentioned, for the initial condition where heating of the fuel sample in the cup 22 begins, the volume of the fuel sample is generally equal to the volume of the cup 22. Thus, the initial value of the electrical capacitance can be used to determine ethanol or MTBE concentration. Steps 114 and 116 are optional. Also, determining the concentration from the first measurement can be done after the heating is over, as to be discussed hereinafter.

Once the ethanol concentration is determined in step 116, the method advances to step 118, where a query is made as to whether the heating is over. The heating is over when the predetermined time duration Δt has passed. Alternatively, the evaporation can end when a predetermined temperature is reached. For example, at 20° C., a temperature increase of only 8° C. may be sufficient to determine the volatility of the fuel sample. Another variable that may be used to determine if the heating should end is the capacitance value. In this aspect, for example, the capacitance value can be compared to a predetermined capacitance value to determine whether the capacitance value has reached the predetermined value, ending the heating. Of course, those with skill in the art easily recognize that there are other choices available to determine when the heating should end.

Returning now to step 114, if the measured voltage and electrical capacitance of step 108 is not the first sampling, then the procedure advances directly to step 118. The procedure would also advance directly to step 118 if the step of determining the oxygenate concentration in 116 is not performed. At step 118, if the heating is not over, then the procedure returns to step 106 where the current through the heater 24 is increased as previously discussed. Then, the remainder of the steps are completed.

Figure 6:
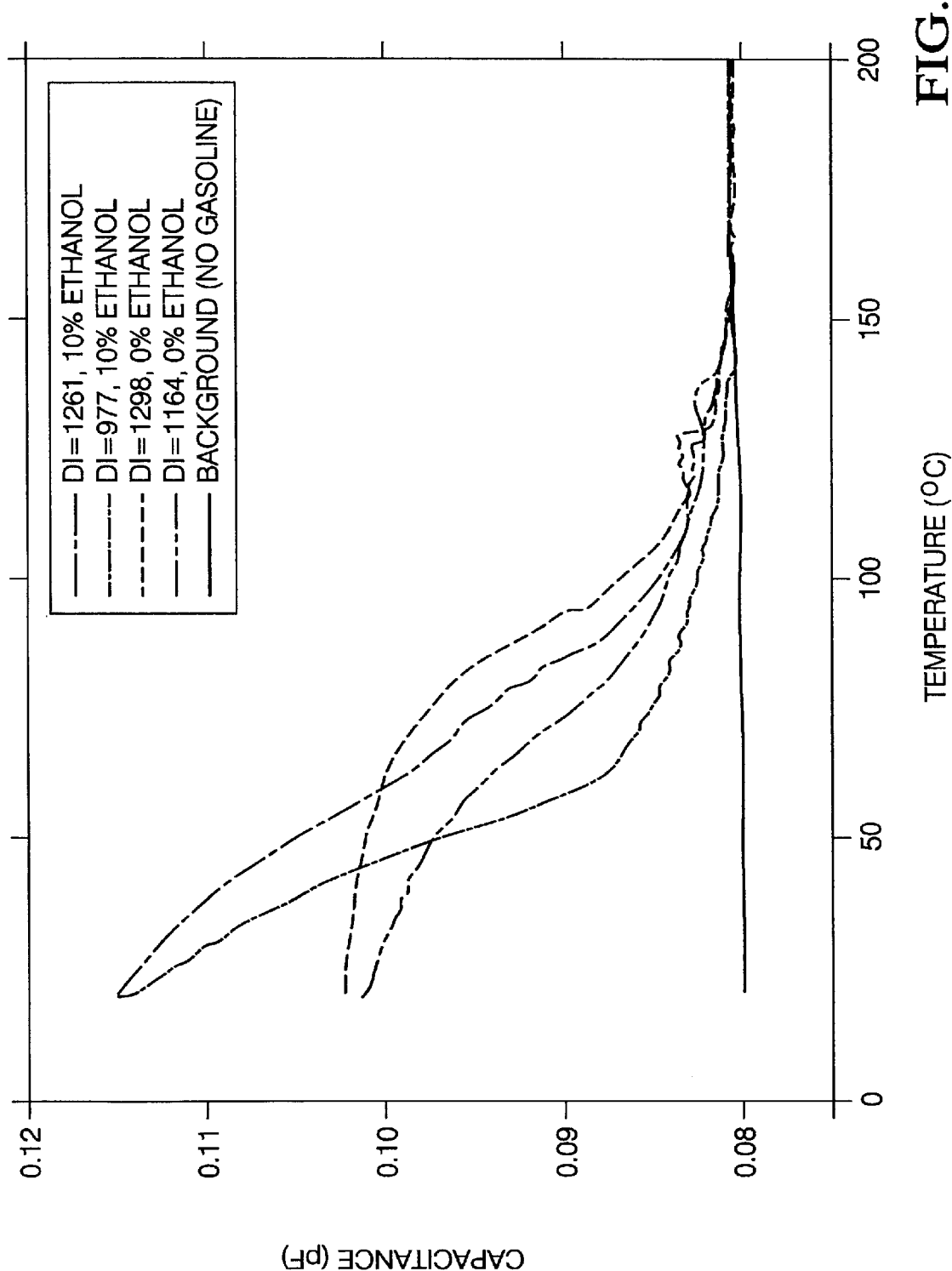
FIG. 6 is a graph comparing capacitance data taken with gasoline fuels that contain 10% ethanol with gasoline that does not contain ethanol.

In step 118, however, if the heating is over, then the current through the heater 48 stops. The procedure advances to step 120 where the results at the different time periods are compared to data for fuels of various volatilities. Optionally, oxygenate concentration can also be determined at this point. FIG. 6 shows a graph of temperature versus capacitance for gasoline fuels of known DI containing 10% ethanol and gasoline without ethanol determined by experimentation. The graph can be used to develop, for example, a lookup table stored in the microcontroller 26 for use in step 120. Alternatively, the values determined by experimentation for temperature and capacitance can be incorporated into equations, which, for example, relate the change in capacitance over a particular temperature range to fuel DI.

Once the driveability index is determined in step 120, it can be stored by the microcontroller 26 and used for engine control upon the next start up in step 122. When the engine starts, the microcontroller 26 sends the DI to the engine controller, and the engine controller would use it to determine the amount of fuel that should be supplied to the engine relative to air intake while the air-to-fuel ratio is controlled open loop prior to engine warm up. The procedure ends at step 124.

While the invention has been described by reference to certain preferred embodiments, it should be understood that numerous changes could be made within the spirit and scope of the inventive concepts described. Accordingly, it is intended that the invention not be limited to the disclosed embodiments, but that it have the full scope permitted by the language of the following claims.

What is claimed is:

1. A method for determining a volatility of a fuel sample, comprising the steps of:

collecting the fuel sample in a container proximate to a heater device;

heating the fuel sample over a time period using the heater device;

measuring a capacitance of the fuel sample periodically during the step of heating the fuel sample;

determining a temperature of the fuel sample periodically during the step of heating the fuel sample; and determining the volatility of the fuel sample using the capacitance and the temperature.

2. The method according to claim 1, further comprising the step of:

shutting off a fuel pump of a vehicle prior to the step of heating the fuel sample.

3. The method according to claim 2, further comprising the step of:

storing a value for the volatility of the fuel sample until an ignition of the vehicle is turned on.

4. The method according to claim 1, wherein the step of collecting the fuel sample in a container comprises the step of:

collecting the fuel sample in a cup mounted on the heater device when a fuel pump is running.

5. The method according to claim 1, wherein the step of heating the fuel sample over a time period using the heater device comprises the step of:

heating the fuel sample until a temperature of the fuel sample reaches a starting temperature plus a temperature change.

6. The method according to claim 1, wherein the step of heating the fuel sample over a time period using a heater device comprises the step of applying current to a heater of the heater device, wherein the heater device further includes:

a dielectric body with a surface on which the container is mounted;

a guard electrode on the surface electrically connected to the container; and two electrodes within the dielectric body operatively positioned to measure the capacitance of the fuel sample in the container; and wherein the heater is disposed within the dielectric body below the two electrodes.

7. The method according to claim 6, wherein the heater is a resistive heater with a known relationship of a resistance of the resistive heater to a heater temperature.

8. The method according to claim 6, further comprising the step of:

operatively coupling a circuit to the two electrodes for measuring the capacitance of the fuel sample.

9. The method according to claim 1, wherein the step of measuring a capacitance of a fuel sample comprises the steps of:

operatively positioning two electrodes to measure the capacitance of the fuel sample in the container; and operatively coupling a circuit to the two electrodes for measuring the capacitance.

10. The method according to claim 1, wherein the step of determining a temperature of the fuel sample comprises the steps of:

operatively coupling a circuit to the heater device for measuring a voltage drop across the heater device;

determining a resistance of the heater device using the voltage drop and a current applied to the heater device; and determining a heater temperature of the heater device based on a known relationship between the resistance of the heater device and the heater temperature; and wherein the heater temperature is the temperature of the fuel sample.

11. The method according to claim 1, wherein the step of determining the volatility of the fuel sample using the capacitance and the temperature comprises the step of:

comparing the capacitance and the temperature to experimental values for fuels with a variety of volatilities.

12. The method according to claim 1, further comprising the step of using a first measurement of capacitance to detect a concentration of an oxygenate in the fuel sample.

13. The method according to claim 1, wherein the step of determining the volatility of the fuel sample comprises the step of determining a driveability index of the fuel sample.

14. An apparatus for determining a volatility of a fuel sample, comprising:

a container for collecting the fuel sample proximate to a heater device, the heater device heating the fuel sample over a time period;

means for measuring a capacitance of the fuel sample periodically during the step of heating the fuel sample;

means for determining a temperature of the fuel sample periodically during the step of heating the fuel sample; and means for determining the volatility of the fuel sample using the capacitance and the temperature.

15. The apparatus according to claim 14, wherein the container is a cup mounted on the heater device collecting the fuel sample when a fuel pump is running.

16. The apparatus according to claim 14, wherein the heater device comprises:

a dielectric body with a surface on which the container is mounted;

a guard electrode on the surface electrically connected to the container;

two electrodes within the dielectric body operatively positioned to measure the capacitance of the fuel sample in the container; and a heater disposed within the dielectric body below the two electrodes.

17. The apparatus according to claim 16, wherein the heater is a resistive heater with a known relationship of a resistance of the resistive heater to a heater temperature.

18. The apparatus according to claim 16, further comprising:

a circuit operatively coupled to the two electrodes for measuring the capacitance of the fuel sample.

19. The apparatus according to claim 14, wherein the means for measuring a capacitance of a fuel sample comprises:

two electrodes operatively positioned to measure the capacitance of the fuel sample in the container; and a circuit operatively coupled to the two electrodes for measuring the capacitance.

20. The apparatus according to claim 14, wherein the means for determining a temperature of the fuel sample comprises:

a circuit operatively coupled to the heater device for measuring a voltage drop across the heater device;

means for determining a resistance of the heater device using the voltage drop and a current applied to the heater device; and means for determining a heater temperature of the heater device based on a known relationship between the resistance of the heater device and the heater temperature; and wherein the heater temperature is the temperature of the fuel sample.

21. The apparatus according to claim 14, wherein the means for determining the volatility of the fuel sample using the capacitance and the temperature comprises:

means for comparing the capacitance and the temperature to experimental values for fuels with a variety of volatilities.

* * * * *